Nov. 22, 1932. G. H. DALRYMPLE Plant Pat. 44
FREESIA
Filed June 2, 1932
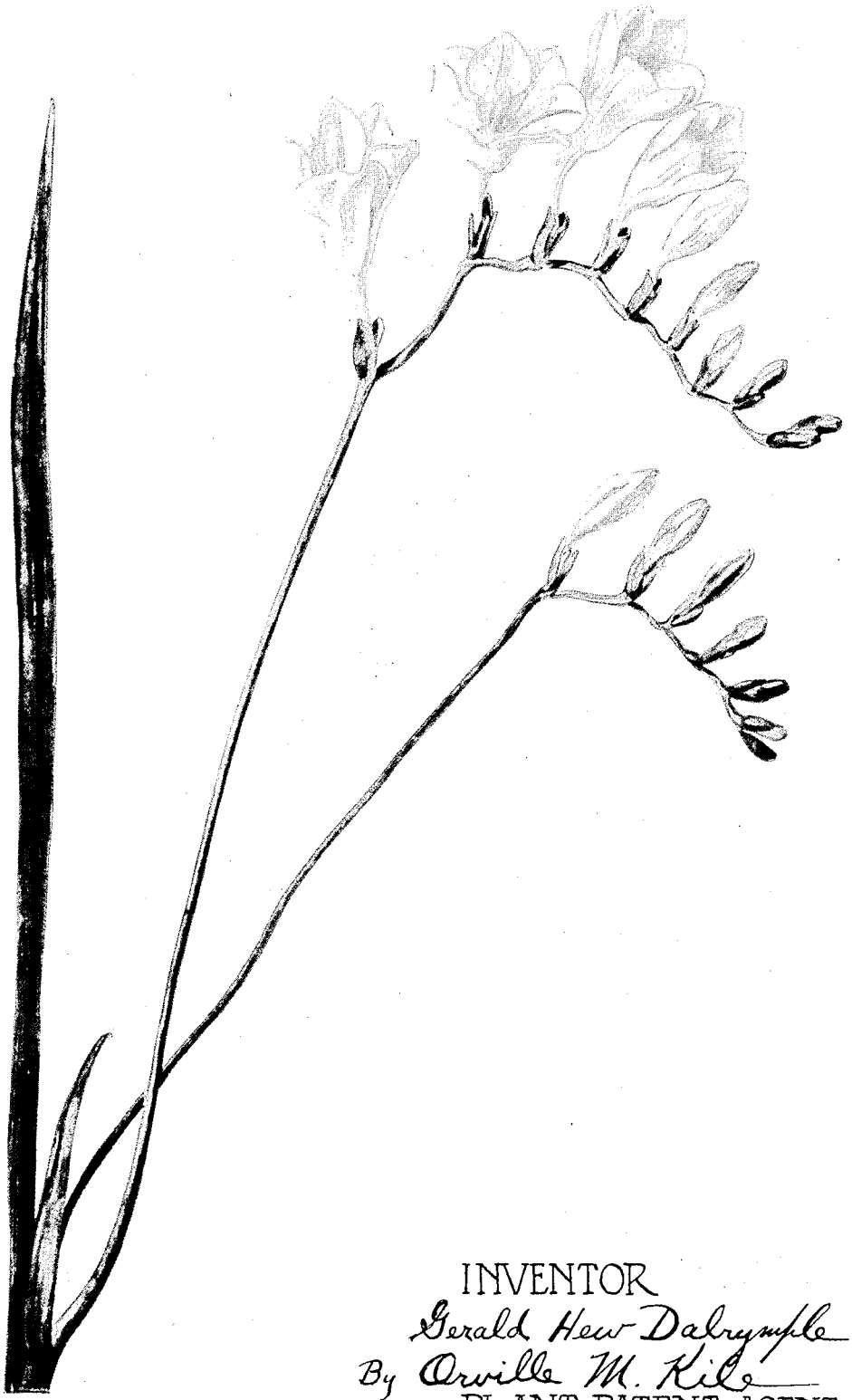
INVENTOR
Gerald Hew Dalrymple
By Orville M. Kile
PLANT·PATENT·AGENT Patented Nov. 22, 1932

Plant Pat. 44

UNITED STATES PATENT OFFICE

GERALD HEW DALRYMPLE, OF BARTLEY, NEAR SOUTHAMPTON, ENGLAND, ASSIGNOR TO C. J. VAN BOURGONDIEN, OF BABYLON, NEW YORK

FREESIA

Application filed June 2, 1932. Serial No. 615,053.

My invention relates to improvements in tinted or colored freesias. The object of my invention in general is to provide a freesia of the general type mentioned, having large blossoms, many flowers on a single spike, a goodly number of which open at one time, having an orange color heretofore unknown in freesias, having a profusion of flowers on long stems and certain desirable growth characteristics hereinafter described.

My new freesia was first produced by crossing two un-named yellow seedlings and selecting from the results of this cross. After reproducing this new variety for several years and testing it thoroughly, I sold the entire stock of this variety in the fall of 1930 to Mr. C. J. Van Bourgondien, of Babylon, New York, United States of America, who took this stock to his home on Long Island and as late as April 20, 1932 still owned and had in his possession the entire stock. No bulbs having been sold.

The accompanying illustration shows (in the originals) in approximately natural size and colors a flower spike of my new freesia at the cutting stage, and another flower spike from the same general branch in a less mature stage. The second blossom from the left, on the upper spike, may be considered to be the typical form of blossom. The others are either too far advanced or not yet fully opened, as is always true of any flower spike where the individual blossoms open up successively. Two leaves are also shown.

The following is a detailed description of this new variety of freesia:

*Flowers.*—Nine to ten flowers ordinarily are found on a single spike, although their number will vary with the condition of the plant. The flowers are borne upright along an irregularly jointed axis which is abruptly bent at right angles to the supporting vertical stem or peduncle. The first blossom on a prime spike is ordinarily located about 1¼ inches below the second blossom, the latter marking the point at which the right-angular turn of the flower spike is most prominent.

The flowers when fully opened measure 1¼ to 1½ inches across the top and from the point of attachment to the axis to the top of the flower the usual measurement is about 2½ inches.

The perianth is funnel-shaped, long and gracefully tapering, the six lobes or segments at the top of the perianth turning back when fully opened so as to give a desirable display of color, but not opening to a position so nearly at right angles to the tube as is found in other varieties. Four flowers on a spike are open at one time, another partly opened, and at least two more buds showing the orange color.

This variety has a sweet, peculiarly pungent but pleasing odor.

Three white anthers are prominently displayed in the throat of the flower and the single pistil has a six-branched top. Considerable pollen is visible down in the tube of a mature flower.

*Color:*—The dominant color tone is orange. The darkest portions of the petal lips are "cadmium orange", the medium shades "orange", and the lighter portions "deep chrome", using these color terms as shown in Ridgway's Color Standard and Nomenclature, edition of 1912, Plate III. Some of the lighter shades on the lower part of the tube, as shown in the original illustration, are "lemon chrome" (Plate IV of Ridgway's). Each petal lip has a narrow dark stripe down its middle reaching down inside the tube. This stripe is ordinarily not visible on the outside.

*Sepals:*—Two in number, loose fitting, about ½ inch long. One sepal has a deep division, giving a two-toothed effect.

*Plant:*—This variety is an extremely vigorous grower and bloomer. The foliage and flowers, under good greenhouse conditions, will reach a height of 36 inches. There are commonly 3 or 4 flowering spikes to each bulb. Owing to its extremely strong and healthy growth, this variety is more resistant to disease than most other varieties.

*Leaves:*—These are usually 12 to 14 inches long when mature and from $\frac{5}{16}$ to ⅜ inches wide at their widest points, except that the sheath-leaves surrounding the base of a flower stem may be opened out to a width of ½ inch. The mature leaves are of a "spinach green" (Plate V—Ridgway's).

The stems are slender but of a sturdy structure and fully capable of holding the heavy flower spikes upright. The color of the stems is light green, ranging from "Coste green" to "lettuce green" (Plate V, Ridgway's). On many of the stems, particularly at the points where the blossoms are attached, a slightly brown shade is found.

*Reproduction* is exceedingly rapid due to the large number of corms produced.

The principal features which I believe distinguish my new variety from all other known varieties of freesias are;

First, its distinctive orange color, something entirely different from the colors heretofore known in freesias.

Second, its large number of flowers displayed on each spike.

Third, its exceptionally vigorous growing and blooming qualities, particularly the usual production of three spikes of flowers from each bulb.

Fourth, its rapidity of reproduction.

Fifth, its resistance to diseases.

What I claim as new is:

The variety of freesia herein shown and described, characterized particularly by its large orange colored flowers, profuse growth and blooming habits and rapidity of reproduction.

G. H. DALRYMPLE.